United States Patent [19]

Junek et al.

[11] 4,350,816
[45] Sep. 21, 1982

[54] PROCESS FOR THE PRODUCTION OF 4-AMINO-6-HYDROXY-3-PHENYL ISOXAZOLO [5,4-B] PYRIDINE-5-CARBONITRILES

[75] Inventors: Hans Junek; Burkhard Thierrichter, both of Graz, Austria

[73] Assignee: Lonza Ltd., Gampel, Switzerland

[21] Appl. No.: 209,149

[22] Filed: Nov. 21, 1980

[30] Foreign Application Priority Data

Nov. 22, 1979 [CH] Switzerland .................. 10409/79

[51] Int. Cl.³ .......................................... C07D 498/04
[52] U.S. Cl. .................................................. 546/116
[58] Field of Search ............................. 546/115, 116

[56] References Cited

U.S. PATENT DOCUMENTS

| | | | |
|---|---|---|---|
| 3,381,016 | 4/1968 | Markillic | 260/296 |
| 3,736,325 | 5/1973 | Denzel et al. | 546/115 |
| 3,736,326 | 5/1973 | Denzel et al. | 546/115 |
| 3,736,327 | 5/1973 | Denzel et al. | 546/115 |
| 3,825,535 | 7/1974 | Denzel et al. | 546/115 |
| 3,912,737 | 10/1975 | Denzel et al. | 546/115 |
| 3,985,760 | 10/1976 | Hoehn | 546/115 |

OTHER PUBLICATIONS

Quilico et al., Rend. Ist. Lambardo Sci., 69, 1936, pp. 439 to 457.
Quilico et al., Gazz. Chim. Ital., 67, 1937, pp. 589 to 603.
Chemical Abstracts, vol. 78, 4235p.
Chemical Abstracts, vol. 78, 4236q.
Chemical Abstracts, vol. 78, 16162a.
Chemical Abstracts, vol. 80, 82964f.
Chemical Abstracts, vol. 85, 21450s.
W. Janssen and T. Denzel, Arch. Pharmaz., 308, (1972), pp. 471–479.
T. Denzel and H. Höhn, Arch. Pharmaz., 305, (1972) pp. 833–839.

*Primary Examiner*—John M. Ford
*Attorney, Agent, or Firm*—Fisher, Christen & Sabol

[57] ABSTRACT

Process for the production of 4-amino-6-hydroxy-3-aryl isoxazolo [5,4-b] pyridine-5-carbonitriles having the formula:

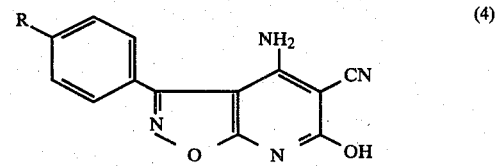

wherein R (a) is —H, (b) is —Cl or (c) is —CH₃. 3-Amino-2,4,dicyanocrotonic acid methyl ester having the formula:

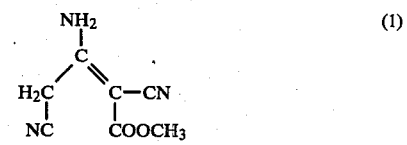

is reacted with a benzohydroxyamino acid chloride having the formula:

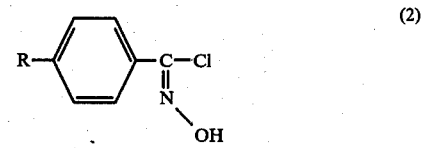

wherein R has the same meaning as above, in the presence of a strong base (at least molar) at a temperature of up to 10° C. to produce, as an intermediate, the corresponding 3-amino-2-cyano-3-(5-amino-3-aryl-isoxazol-4-yl)-acrylic acid methyl ester having the formula

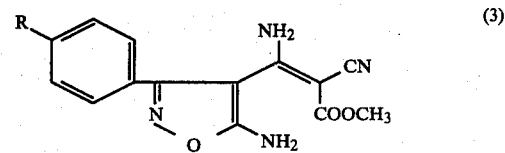

wherein R has the same meaning as above. The intermediate product is reacted in excess diluted NaOH or KOH at a temperature of 50° to 110° C. to produce the corresponding 4-amino-6-hydroxy-3-aryl-isoxazolo [5,4-b] pyridine-5-carbonitrile.

8 Claims, No Drawings

PROCESS FOR THE PRODUCTION OF 4-AMINO-6-HYDROXY-3-PHENYL ISOXAZOLO [5,4-B] PYRIDINE-5-CARBONITRILES

BACKGROUND OF THE INVENTION

1. Field of This Invention

This invention involves the production of isoxazolo[5,4-b]pyridine-5-carbonitriles.

2. Prior Art

Various processes for the synthesis of isoxazolo[5,4-b]pyridines are known. Two of such processes start out with 5-amino-isoxazoles, which are cyclized with β-ketoesters or 1,3-diketones (U.S. Pat. No. 3,381,016) or are reacted with alkoxy methylene malonic or acetic acid esters into enamines and are subsequently subjected by heating in diphenyl ether or polyphosphoric acid to cyclization [T. Denzel and H. Hoehn, Arch. Pharmaz, 305, 833 (1972), and W. Janssen and T. Denzel, Arch. Pharmaz, 308, 471 (1975)].

Benzohydroxyamino acid chlorides were used for the first time as starting compounds for the production of isoxazoles by Quilico et al., Rend. ist. lombardo sci. 69, 439 (1936), and Quilico et al., Gazz. chim. ital. 67, 589 (1937), in the case of reaction with β-diketones, β-ketoaldehydes, β-ketoesters, malonic esters, cyano acetic ester and cyano ketones. It is particularly mentioned that the reactions with cyano acetamide and cyano acetic ester lead to 3,4,5-trisubstituted isoxazoles.

BROAD DESCRIPTION OF THIS INVENTION

An object of this invention is to provide for the production of 4-amino-6-hydroxy-3-phenyl isoxazolo[5,4-b]pyridine-5-carbonitriles in a simple manner. Other objects and advantages of this invention are set out herein or are obvious herefrom to one ordinarily skilled in the art.

The objects and advantages of this invention are achieved by the process of this invention.

This invention involves a process for the production of 4-amino-6-hydroxy-3-aryl-isoxazolo[5,4-b]pyridine-5-carbonitriles having the formula:

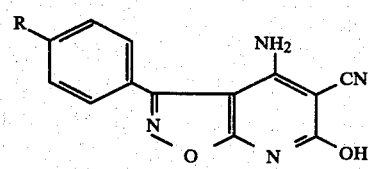

wherein R (a) is —H, (b) is —Cl or (c) is —CH₃. 3-Amino-2,4-dicyanocrotonic acid methyl ester having the formula:

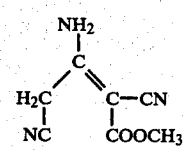

is reacted with a benzohydroxyamino acid chloride having the formula:

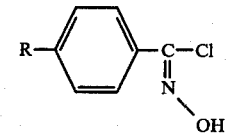

wherein R has the same meaning as above, in the presence of a strong base (at least molar) at a temperature of up to 10° C. to produce, as an intermediate, the corresponding 3-amino-2-cyano-3-(5-amino-3-aryl-isoxazol-4-yl)-acrylic acid methyl ester having the formula:

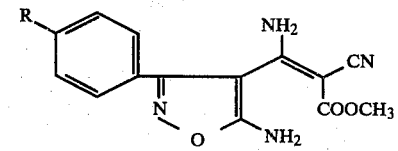

wherein R has the same meaning as above. The intermediate product is reacted in excess diluted NaOH, or KOH at a temperature of 50° to 110° C. to produce the corresponding 4-amino-6-hydroxy-3-aryl-isoxazolo[5,4-b]pyridine-5-carbonitrile. Cyclization of intermediate compound (3) occurs.

Preferably the strong base is sodium methylate in methanol, or sodium ethylate in ethanol or aqueous sodium hydroxide. Preferably the first reaction step is conducted in water. Preferably, in the first reaction step, 10 to 20 ml. of the solvent or suspending agent is used per gram of the starting cyanocrotonic acid methyl ester. Preferably the second reaction step is conducted in water or an alcohol. Also, preferably 30 to 40 ml of the solvent or suspending agent is used per gram of intermediate product (3).

By way of summary, this invention involves a process for the production of 4-amino-6-hydroxy-3-aryl-isoxazolo[5,4-b]pyridine-5-carbonitriles from 3-amino-2,4-dicyanocrotonic acid methyl ester and benzohydroxamic acid chloride by way of 3-amino-2-cyano-3-(5-amino-3-aryl-isoxazol-4-yl)-acrylic acid methyl ester as an intermediate product.

This invention also includes the intermediate ester (3).

DETAILED DESCRIPTION OF THIS INVENTION

Any suitable strong base can be used. Examples of useful alkali metal and alkaline earth metal carbonate basic agents are sodium carbonate, potassium carbonate, magnesium carbonate, cesium carbonate, barium carbonate, radium carbonate, calcium carbonate, strontium carbonate, beryllium carbonate, rubidium carbonate and lithium carbonate. Another useful carbonate is ammonium carbonate. Examples of useful alkali metal and alkaline earth hydroxide basic agents are sodium hydroxide, potassium hydroxide, potassium hydroxide, magnesium hydroxide, calcium hydroxide, barium hydroxide, strontium hydroxide, berylium hydroxide, cesium hydroxide and lithium hydroxide. Another useful hydroxide is ammonium hydroxide. Examples of useful alkali metal or alkaline earth metal alcoholates or alkoxides basic agents are sodium methoxide, sodium ethoxide and magnesium methoxide. Examples of useful alkali metal or alkaline earth metal oxide basic agents are sodium monoxide, potassium monoxide, magnesium oxide, barium oxide, strontium oxide, calcium oxide, berylium oxide, cesium oxide, rubdium oxide and lithium oxide. The preferred strong bases are sodium methylate or ethylate dissolved in methanol or ethanol, respectively, and aqueous sodium hydroxide. (Sodium methylate is sodium methoxide, and sodium ethylate is sodium ethoxide.) Mixtures of bases can be used.

The first step of the reaction can be carried out in water or alcohol, for example, a $C_1$ to $C_4$ alcohol, such as, methanol, ethanol, propanol, isopropanol and butanol. Methanol and ethanol are the preferred alcohols. The quantity of solvent or suspension agent is not critical; preferably 10 to 20 ml of solvent or suspending agent per gram of starting material (1) is used in the first reaction step. Mixtures of solvents and/or suspending agents can be used.

The second step of the reaction is preferably conducted in water, but any of the above enumerated solvents or suspending agents can be used. The quantity of solvent or suspending agent is not critical; preferably 30 to 40 ml. of the solvent or suspending agent is used per gram of intermediate product (3) in the second reaction step. Mixtures of solvents and/or suspending agents can be used.

The product of this invention, namely, 4-amino-6-hydroxy-3-phenyl isoxazolo[5,4-b]pyridine-5-carbonitrile is useful as a tranquilizer, an antiinflammatory agent, an antiasthmatic agent (Chemical Abstracts 78, 4236Q, 4235P and 16162A, Chemical Abstracts 80, 82964F, and Chemical Abstracts 85, 21450S) or for plant grow regulation (Chemical Abstracts 84, 59279K). Also utility by analogy is involved.

EXAMPLE 1

3-Amino-2-cyano-3-(5-amino-3-aryl-isoxasole-4yl)-acrylic acid methyl ester (3a-c)

1.1 g (6.7 mmole) of compound (1) is dissolved in 15 ml of sodium methylate solution (0.15 g of Na in 15 of MeOH) and is cooled down to 0° C. Then 1.0 g (6.45 mmole) of compound (2a) or 1.3 g (6.84 mmole) of compound (2b) or 1.1 g (6.8 mmole) of compound (2c) is dissolved in 6 ml of MeOH, and is added drop by drop to the solution while stirring so slowly that the temperature of the solution does not rise above 10° C. After completion of the drop by drop addition, stirring is still continued for 10 minutes, while cooling with ice. Then the solution is stirred for 1.5 hours at ambient temperature. The precipitate is sucked off (removed), washed with MeOH, digested with acetic acid or condensed HCl, again sucked off (removed), and washed with a large amount of MeOH.

Compound (3a): 3-Amino-2-cyano-3-(5-amino-3-phenyl-isoxazole-4-yl)-acrylic acid methyl ester.

Yield: 1.0 g (55 percent) colorless crystals, from DMSO/$H_2O$, having a melting point of 256° C.

| $C_{14}H_{12}N_4O_3$ (284.3) | | | |
| --- | --- | --- | --- |
| | C, percent | H, percent | N, percent |
| Calculated: | 59.14 | 4.26 | 19.71 |
| Found: | 58.27 | 4.30 | 19.29 |

IR(KBr): 3420, 3370, 3310, 3200 ($NH_2$), 2230 (CN), 1675 ($COOCH_3$), 1635, 1595 (C=C) $cm^{-1}$.

$^1$H-NMR(DMSO): 3.63 (s,—$OCH_3$), 4.25 (s,—$NH_2$), 7.36 (S,Aromat.), 8.60 (d-$NH_2$) ppm.

Compound (3b): 3-amino-2-cyano-3-[5-amino-3-(p-chlorophenyl)-isoxazole-41yl]-acrylic acid methyl ester.

Yield: 1.1 g (52 percent) of colorless crystals having a melting point of 164° C.

| $C_{14}H_{11}N_4O_3Cl$ (318.7) | | |
| --- | --- | --- |
| | C, percent | H, percent |
| Calculated: | 52.76 | 3.48 |
| Found: | 52.15 | 3.61 |

IR(KBr): 3380, 3240 ($NH_2$), 2210 (CN), 1680 ($COOCH_3$), 1640 (C=C) $cm^{-1}$.

Compound (3c): 3-Amino-2-cyano-3-[5-amino-3-(p-tolyl)-isoxazol-4-yl]-acrylic acid methyl ester.

Yield: 1.0 g (52 percent) of colorless crystals having a melting point of 183° C.

| $C_{15}H_{14}N_4O_3$ (298.3) | | | |
| --- | --- | --- | --- |
| | C, percent | H, percent | N, percent |
| Calculated: | 60.40 | 4.73 | 18.58 |
| Found: | 60.24 | 4.58 | 18.54 |

IB(KBr): 3360, 3200 ($NH_2$), 2960 (CH), 2210 (CN), 1680 ($COOCH_3$), 1640 (C=C) $cm^{-1}$.

$^1$H-NMR (DMSO): 2.32 (s,—$CH_3$), 3.61 (s,—$OCH_3$), 7.20 (q,Aromat.), 8.51 (s,—$NH_2$), 8.81 (s,—$NH_2$) ppm.

EXAMPLE 2

4-Amino-6-hydroxy-3-phenyl-isoxazolo[5,4-b]pyridine-5-carbonitrile (4a)

0.5 g (1.76 mmole) of 3-amino-2-cyano-3-(5-amino-3-phenyl-isoxazol-4-yl)-acrylic acid methyl ester [compound (3a)] is dissolved in 7 ml of 2 N NaOH and 10 ml of EtOH, and is heated to boiling for 3 hours. Then the undissolved residue is filtered off. Colorless plates are precipitated during cooling off, which are sucked off (removed) and washed with a small amount of MeOH.

Yield: 0.3 g (62 percent) of colorless plates, from crystalline acid, having a melting point of 251° C.

| $C_{13}H_8N_4O_2$ (252.2) | | | |
| --- | --- | --- | --- |
| | C, percent | H, percent | N, percent |
| Calculated: | 61.90 | 3.20 | 22.21 |
| Found: | 61.61 | 3.24 | 22.20 |

IR(KBr): 3440, 3360, 3250 (NH, $NH_2$), 2210 (CN), 1650 (C=O), 1590 (C=C) $cm^{-1}$.

EXAMPLE 3

4-amino-6-hydroxy-3-tolyl-isoxazolo[5,4-b]pyridine-5-carbonitrile (4c)

10. g (3.35 mmole) of 3-amino-2-cyano-3-[5-amino-3-(p-tolyl)-isoxazolo-4-yl]-acrylic acid methyl ester [compound (3c)] is dissolved in 14 ml of 2 N NaOH and 20 ml of EtOH. The batch is heated to boiling for 3 hours. At the same time a precipitate is already deposited, which after cooling is sucked off (removed) and washed with MeOH.

Yield: 0.5 g (56 percent) of colorless crystals, from crystaline acid, having a melting point of 240° C.

| C₁₄H₁₀N₄O₂ (266.3) | | | |
|---|---|---|---|
| | C, percent | H, percent | N, percent |
| Calculated: | 63.15 | 3.79 | 21.04 |
| Found | 62.35 | 4.05 | 20.47 |

IR(KBr): 3500, 3380, 3260 (NH$_2$), 2215 (CN), 1650 (C=O), 1580 (C=C) cm$^{-1}$.

What is claimed is:

1. Process for the production of 4-amino-6-hydroxyl-3-aryl-isoxazolo[5,4-b]pyridine-5-carbonitrile having the formula:

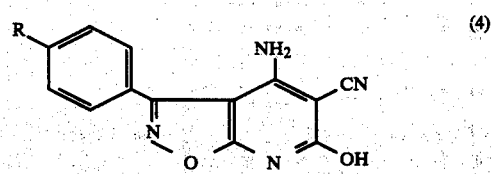
(4)

whereby R (a) is —H, or (b) is —Cl or (c) is —CH$_3$, comprising (A) reacting 3-amino-2,4-dicyanocrotonic acid methyl ester having the formula:

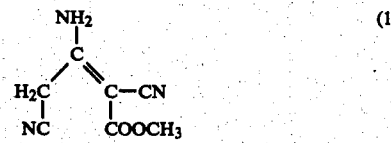
(1)

with a benzohydroxyamino acid chloride having the formula:

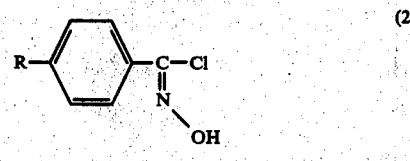
(2)

wherein R has the same meaning as above, in the presence of a strong base at a temperature of up to 10° C. to produce, as an intermediate, the corresponding 3-amino-2-cyano-3-(5-amino-3-aryl-isoxazol-4yl)-acrylic acid methyl ester having the formula:

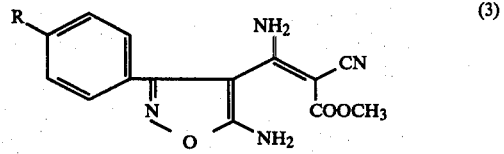
(3)

wherein R has the same meaning as above; and (B) reacting said intermediate product (1) in excess diluted NaOH or KOH at a temperature of 50° to 110° C. to produce the corresponding 4-amino-6-hydroxy-3-aryl-isoxazolo[5,4-b]pyridine-5-carbonitrile.

2. Process as claimed in claim 1 wherein the strong base is sodium methylate in methanol, or sodium ethylate in ethanol or aqueous sodium hydroxide.

3. Process as claimed in claim 1 wherein the first reaction step is conducted in water or an alcohol.

4. Process as claimed in claim 1 wherein the first reaction step is conducted in methanol or ethanol.

5. Process as claimed in claim 1 wherein, in the first reaction step, 10 to 20 ml of the solvent or suspending agent is used per gram of the starting cyanocrotonic acid methyl ester.

6. Process as described in claim 1 wherein the second reaction step is conducted in water or an alcohol.

7. Process as described in claim 1 wherein 30 to 40 ml of the solvent or suspending agent is used per gram of intermediate product (3).

8. 4-Amino-6-hydroxyl-3-aryl-isoxazolo[5,4-b]pyridine-5-carbonitrile having the formula:

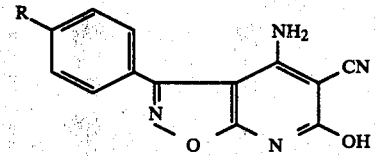

wherein R is —Cl or (b) is —CH$_3$.

* * * * *